US00PP09201P

United States Patent [19]

Egger et al.

[11] Patent Number: Plant 9,201

[45] Date of Patent: Jul. 18, 1995

[54] ORIENTAL LILY PLANT NAMED 'VANITY'

[75] Inventors: Donald L. Egger, Aurora; Edward A. McRae, Sandy; Ted T. Kirsch, Myrtle Point, all of Oreg.

[73] Assignee: Cebeco Lilies, Inc., Aurora, Oreg.

[21] Appl. No.: 255,150

[22] Filed: Jun. 13, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Klarquist, Sparkman, Campbell, Leigh & Whinston

[57] ABSTRACT

A new and distinct Oriental lily hybrid named 'Vanity' characterized by numerous large, upright, rose pink flowers and forming a striking inflorescence with tall, strong stems for cut flower production.

1 Drawing Sheet

BACKGROUND OF THE INVENTION

The present invention comprises a new and distinct cultivar of Lilium hybrid, referred to commercially as an upright Oriental lily hybrid, hereinafter sometimes referred to by the cultivar name 'Vanity'.

This invention is the product of a controlled breeding program in Aurora, Oreg. The seed parent was an unnamed, non-released proprietary seedling. This seed parent was mass pollinated with the pollen from several proprietary non-released parents. Both parents were from distantly related upfacing oriental lily lines and the crosses were made in an attempt to fix the upfacing trait into a plant with good cut flower potential.

The 'Vanity' lily has not been observed under all possible environmental conditions. The phenotype may vary significantly with variations in environment such as temperature, light intensity, and day length, without, however, any variation in genotype. The following traits have been repeatedly observed in asexually propagated progeny and are determined to be the basic characteristics of this invention which in combination distinguish this lily as a new and distinct cultivar: (1) floriferous habit; (2) large, upright, rose pink flowers; (3) vigorous growth habit; (4) large buds; (5) tall, strong stems; (6) virus resistance; (7) desirable forcing time. Bulbs of this plant may be precooled and forced out of season for very uniform cut flower production.

The primary distinguishing features of the 'Vanity' lily are its' large numerous rose pink flowers. Compared to Lilium 'Acapulco', this invention has a similar color, as uniform a growth habit, and similar height and stem strength. The invention is earlier by ten days when forced under commercial conditions. It is more virus resistant and has a higher bud count.

Asexual reproduction of this new variety has been accomplished by scaling and tissue culture which was initially performed at Aurora, Oreg. The resulting plants have shown that the above mentioned unique characteristics are firmly fixed and are retained through successive generations reproduced by asexual reproduction.

Figure 2:
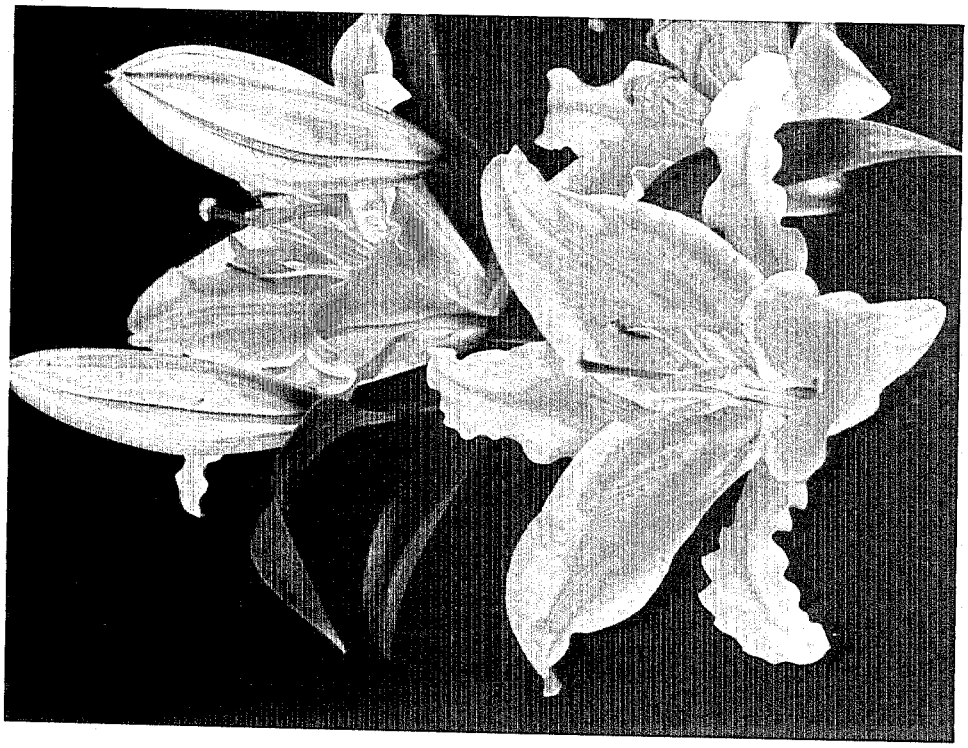
FIG. 2 is a close-up photograph which illustrates in greater detail flowers of the new plant.
Figure 1:
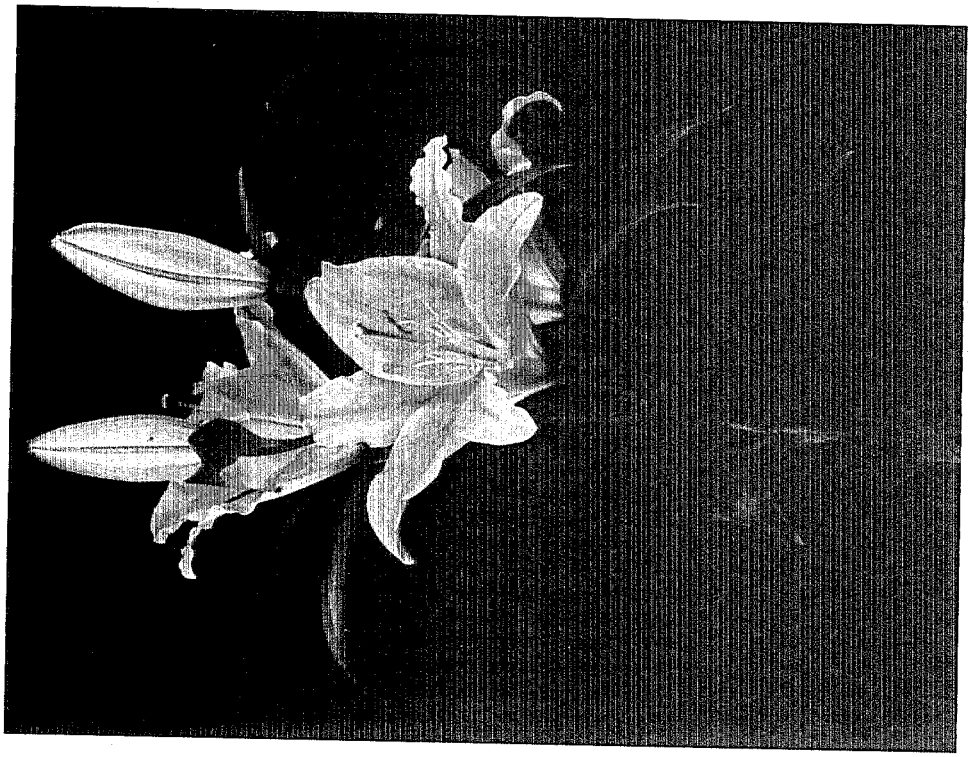
FIG. 1 is a photograph showing 'Vanity' lily.

The photographs of the drawing were taken in August 1993 in a studio and illustrate the typical flower and foliage form, with color being as true as is reasonably possible in this type of color photograph.

DETAILED DESCRIPTION

The following is a detailed description of the 'Vanity' lily based on plants produced under commercial practices in greenhouses in Aurora, Oreg. in July 1993. Color references are made to the Royal Horticultural Society Colour Chart (RHS), except where the context indicates a term having its ordinary dictionary meaning.

THE PLANT

Origin: Seedling.

Parentage:

*Seed parent.*—Unnamed seedling.

*Pollen parent.*—Unknown.

Commercial classification: Upright Oriental lily cultivar.

Classification: Division IV. Oriental Hybrid Lily. Subdivision b. Bowl shaped flowers, according to the Horticultural Classification of Lilies by the Royal Horticultural Society of London.

Form: Single erect stem bearing terminal cluster of large flowers.

Height: Variable, about 87 cm, from the top of the soil to the top of the inflorescence.

Growth habit: Vigorous, upright and rigid.

Foliage:

*Arrangement.*—Spiral.

*Quantity.*—Average to abundant with the internode length being 8–20 mm. on one young plant growing in a Cebeco, Inc. greenhouse in Aurora, Oreg., and observed in the fall of 1994.

*Leaf size.*—Variable to about 16 cm long and about 4.5 cm wide.

*Leaf shape.*—Varies from ovate to lanceolate near the top of the stem to elliptic at the stem base.

*Texture.*—Leathery.

*Aspect.*—Glossy.

*Color.*—Very deep green both sides, closest to Green Group 147A with the top of the leaves being somewhat darker and the bottom of the leaves being somewhat grayer.

Bulbs:

*Size.*—Variable, ranging from 14 cm to about 20 cm in circumference for commerical use.

*Color.*—White.

THE BUD

Size: Very large, to about 12 cm long and 4.5 cm wide just prior to opening.

Shape: Ovoid with apex commonly having three obtuse tips.

Rate of opening: The mature bud opens slowly in response to light.

Color: Yellow green, blushed with Red-Purple Group 64A.

THE FLOWER

Blooming habit: Annually, once and profusely, mid-season.

Days to bloom: Flowers approximately 95 to 110 days after spring greenhouse planting under typical commercial flower forcing conditions of 17° C. night time temperatures.

Inflorescence size: About 37 cm high and 35 cm wide when there are five flowers present.

Flower size: Very large.

*Diameter.*—To about 20 cm.

*Depth.*—About 10 cm.

Borne: Raceme of about five flowers from bulbs of about 16 cm. in circumference.

Shape: When the flower first opens it is cup-shaped. Later, the shape flattens out and the tepals reflex at the tips.

Tepalage:

*Number.*—Six.

*Arrangement.*—Imbricated.

*Texture.*—Waxy.

*Aspect.*—Satiny, glossy.

*Margins.*—Undulate, especially outer tepals.

*Size.*—Length: About 14 cm. Width: Inner tepals — about 7.2 cm. Outer tepals — about 4 cm. Depth of imbrication: About 3 cm.

*Nectary.*—Light green (Yellow-Green Group 145A), smooth, oozing, 5 cm long, surrounded with yellow gold (Yellow Group 9A).

*Projections.*—Simple, papillate, red purple, covering bottom two-thirds of tepal to halfway down nectary.

*Spots.*—Oval shaped, all papillate, red purple (Greyed-Purple Group 187A), on bottom two-thirds of tepal.

*Blush.*—None.

*Color.*—The intensity of the tepal color fades progressively from the central tepal portions to the margins. Young tepals upperside: Red-Purple Group 64A. Center along midrib: Red-Purple Group 60A. Spots — Greyed-Purple Group 187A. Tepals bottomside: Greyed-Purple Group 186C. Older tepals: Greyed slightly.

*Fragrance.*—Heavy.

*Lasting quality.*—Excellent; under trial conditions at Cebeco Lilies, Inc., in Aurora, Oreg., in 1993, individual flowers lasted from 6–8 days.

Pedicle:

*Length.*—Usually about 10 cm.

*Color.*—Yellow-green (Green Group 137C), mottled with lighter green spots and greyed-purple blotches (Greyed-Purple Group 187A).

*Orientation.*—Ascending upwardly off the stem to about 45° from the horizontal, then curves to vertical to hold flowers upright.

THE REPRODUCTIVE ORGANS

Stamens:

*Number.*—Six, typical of the genus Lilium.

*Anthers before dehiscence.*—Size: To about 41 mm from mature bud. Color: Rose brown. Greyed-Purple Group 184B.

*Filaments.*—Length: about 8.5 cm. Color: Yellow-Green Group 150A at tip to Yellow-Green Group 150D at base.

*Pollen.*—Color: Orange. Greyed-Orange Group 169A.

Pistil:

*Number.*—One.

*Style.*—Length: About 7 cm. Color: Yellow-Green Group 144A on top half. Bottom half, Yellow-Green Group 144C, mottled with Greyed-Purple Group 187C spots.

*Stigma.*—Color: Greyed-Green Group 195A.

THE FRUIT

Fertility: The fruit is fertile.

Shape: Ovoid.

Color at maturity: Soft Brown.

I claim:

1. A new and distinct Oriental lily plant substantially as herein shown and described.

* * * * *